United States Patent [19]

Detsch

[11] Patent Number: 4,911,641
[45] Date of Patent: Mar. 27, 1990

[54] BONE GROWING METHOD AND COMPOSITION

[76] Inventor: Steven G. Detsch, 4115 The Hill Rd., Bonita, Calif. 92002

[21] Appl. No.: 159,126

[22] Filed: Feb. 23, 1988

[51] Int. Cl.$^4$ ............................................. A61C 8/00
[52] U.S. Cl. ................................ 433/228.1; 433/226; 424/435
[58] Field of Search ........................... 433/215–228.1; 424/422, 435

[56] References Cited

U.S. PATENT DOCUMENTS 4,738,623  4/1988  Driskell .............................. 433/173

Primary Examiner—Nancy A. Swisher
Attorney, Agent, or Firm—Michael W. York

[57] ABSTRACT

A method and composition for promoting the growth of bone that are particularly useful in treating bone defects in the human jaw. The method includes surgically exposing the bony defect, cleaning the defect and adjacent teeth, and implanting the composition in the bony defect. The bone growing composition includes two sizes of Hydroxyapatite for supporting the growth of new bone, Tetracycline for its antibiotic effect, freeze dried decalcified human bone for promoting bone growth, and Fibronectin for promoting connective tissue generation and for jelling the bone growing composition.

12 Claims, 3 Drawing Sheets

BONE GROWING METHOD AND COMPOSITION

BACKGROUND OF THE INVENTION

It has been known for a long time that broken bones in man or in animals will heal themselves or grow together if the broken pieces are relatively intact and if they are located closely adjacent each other so that the broken portions are in appropriate contact with each other. This occurs because new bone grows to fill the joint between the broken portions so that the bone portions are reunited and a single united bone results.

This bone growth does not occur if the bone at the location where the bone is broken is no longer present due to fragmentation of the bone from the same blow or other accident that caused the broken bone. In such instances, bone does not grow to fill the gap created between the broken bone portions and the bone parts will not be reunited. Some success has occurred in overcoming this lack of bone growth, by inserting another piece of bone or the like between the broken and damaged portions of the bone. This bone growth appears to occur as a result of new bone growing over the bone implant.

Although, bone has been successfully used as a bone graft material in the past, there are a number of problems associated with its use. One of these problems is related to the somewhat limited availability of bone as a graft material. This can be traced to the limited donors of bone and also to problems associated with the storage of the bone. In this connection, it should be noted that the proper storage of bone requires that it be sterilized and maintained in a serile condition until it is used. One method of accomplishing this has been to seal the bone inside an airtight glass tube and to then expose the bone and the glass container to a high dose of radiation. This radiation could come from a Cobalt-60 radiation source or other radiation source. This need for radiation itself is a possible problem since a radiation facility is required and the radiation may alter the bone's ability to have new bone form around it.

One area that is subject to important bone loss is the mouth. Bone loss can occur in the mouth from various causes including trauma. However, the most important causes are from periodontal disease and from the extraction or loss of teeth that causes the surrounding bone to be absorbed or to receed. This loss of bone is important since it can result in the loss of teeth and/or can prevent the suitable use of replacement or artificial teeth. The loss of bone in the mouth is also significant since this occurs in a comparatively large number of people in comparison to the loss or destruction of bone in other portions of the body. The regeneration of bone in the mouth presents physical problems that are usually not present outside the mouth.

Attempts have been made to replace lost bone in the mouth. An example of such an attempt is set forth in U.S. Pat. No. 3,913,229 and involves the use of calcium phosphate as a material to support the growth or regeneration of new tissue and bone. These attempts have not been entirely successful and have not resulted in the desired bone regeneration and reattachment of the regenerated bone to the teeth through an appropriate fiber ligament. This bone growing method and composition overcomes many previous problems and provides improved results. This method and composition is also not restricted to use in the mouth.

SUMMARY OF THE INVENTION

This invention relates to bone growing methods and more particularly to bone growing methods that are particularly useful in the mouth.

It is accordingly an object of the invention to provide a bone growing method that assists in the growth of bone.

It is an object of the invention to provide a bone growing method that effectively promotes the growth of bone.

It is an object of the invention to provide a bone growing method that is easy to use.

It is also an object of the invention to provide a bone growing method that requires no special instruments.

It is an object of the invention to provide a bone growing method that is particularly suited for use in a confined area such as the mouth.

It is an object of the invention to provide a bone growing method that is particularly useful for treating bone loss in the mouth.

It is also an object of the invention to provide a bone growing method that is particularly useful in treating the effects of periodontal disease.

It is also an object of the invention to provide a bone growing method that is particularly useful for successive treatments.

It is an object of the invention to provide a bone growing method that is capable of restoring a greater amount of bone loss.

It is an object of the invention to provide a bone growing method that is particularly useful for restorative cosmetic purposes in the mouth.

It is an object of the invention to provide a bone growing method that is suited for use adjacent to teeth in the mouth.

It is an object of the invention to provide a bone growing method that is useful in reattaching bone to teeth in the mouth.

The invention provides a method of promoting the growth of bone in a living creature that includes providing a graft composition, surgically operating to expose living bone, inserting the graft composition adjacent the living bone and surgically covering the previously exposed living bone and the adjacently located graft composition. The invention is particularly useful in replacing bone in the mouth of a human being.

BRIEF DESCRIPTION OF THE DRAWINGS

The invention will be hereinafter more fully described with reference to the accompanying drawings in which.

DETAILED DESCRIPTION OF THE PREFERRED EMBODIMENTS

Figure 1:
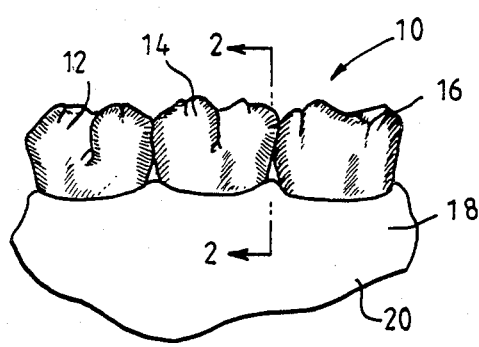
FIG. 1 is an elevational view of a portion of the lower jaw portion of a human mouth.

FIG. 1 is a view of a portion of the human mouth showing the crown portion of the teeth 12, 14, and 16 in side elevation. Surrounding the teeth 12, 14, and 16 is the gingiva 18 and then the adjacent mucosa 20. FIGS. 2 through 16 are sectional views taken substantially on the line 2—2 of FIG. 1.

Figure 2:
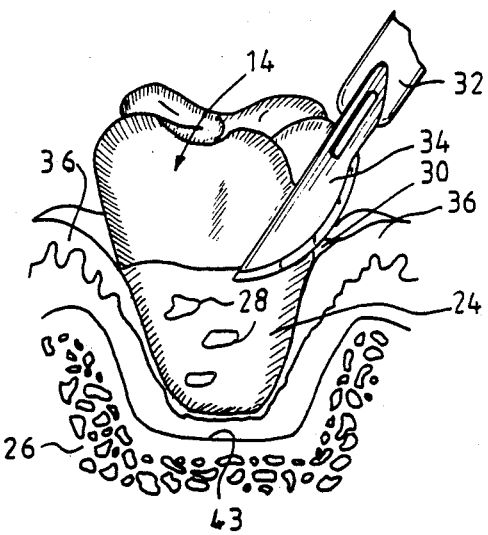
FIG. 2 is a sectional view of a portion of the jaw of the mouth taken substantially on the line 2—2 in FIG. 1 illustrating a step in the practice of the method of the invention and the use of the composition of the invention.

FIG. 2 illustrates the tooth 14 with its tooth crown portion 22 and root portion 24 that is located in bone 26. As illustrated, the root portion 24 has calculus or tartar 28 attached to it. Also, FIG. 2 illustrates the first step in the practice of the method of the invention and the use of the composition of the invention and that is to make an incision 30 in the gingiva 18 in the area to be treated using a scalpel 32 with a number 15 Bard Parker scalpel blade 34. The popillae and gingival tissue 36 is also retracted in the vicinity of the incision 30 to expose the root portion 24 and the attached calculus 28.

Figure 3:
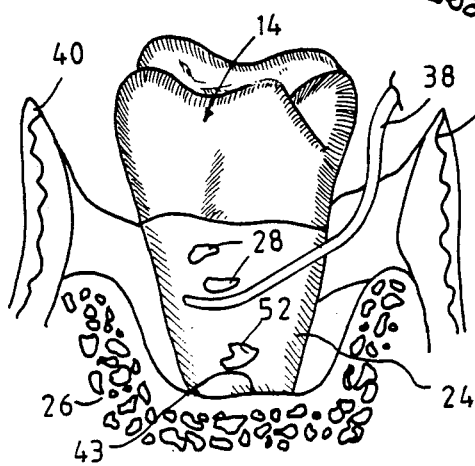
FIG. 3 is a sectional view of the structure illustrated in FIG. 2 illustrating a further step in the practice of the method of the invention and the use of the composition of the invention.

FIG. 3 illustrates the next step in the practice of the method of the invention and in the use of the composition of the invention. As illustrated, the calculus 28 or a substantial amount of the calculus 28 is scraped from the surface of the root portion 24 using a curette 38 known in the art. To accomplish this the gingiva 18 flap edges 40 are retracted. The curette 38 is also used to remove granulation tissue 42 from the flap edges 40. At this time the curette 38 is also used to grossly debride the bony defects such as the defect 43 or an ultrasonic scaler (not shown) could also be used.

Figure 4:
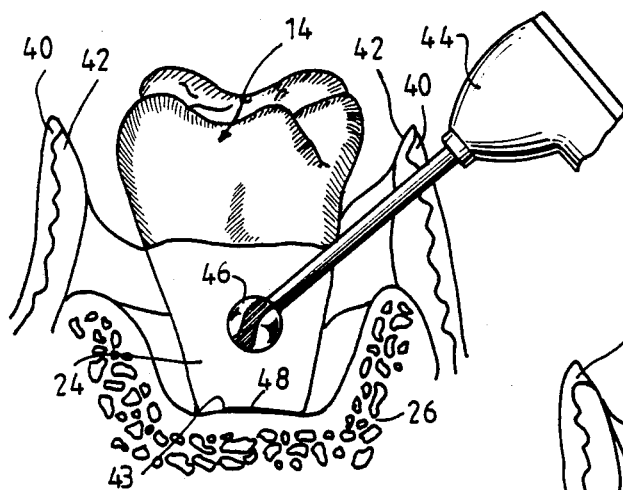
FIG. 4 is a sectional view of the structure set forth in FIGS. 2 and 3 illustrating a further step in the practice of the method of the invention and the use of the composition of the invention.

The next step in the method and the use of the composition of the invention is set forth in FIG. 4. As illustrated, a high speed hand piece 44 is used with a number 6 and a number 1 or 2 round burr 46 to remove residual granulation tissue, epithelia 48 and connective tissue tags down to bone 26.

Figure 5:
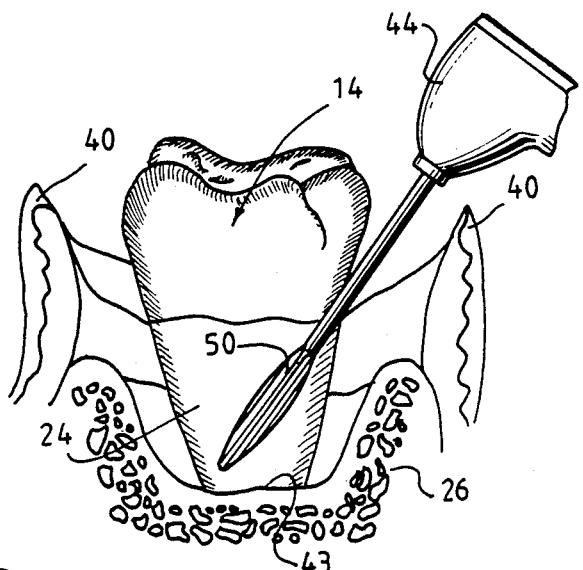
FIG. 5 is a sectional view of the structure set forth in FIGS. 2 through 4 illustrating a further step in the practice of the method of the invention and the use of the composition of the invention.

The next step in the method and the use of the composition of the invention is to use the high speed hand piece 44 with a 12–20 fluted finishing burr 50 to remove surface cementum 52 from the exposed root portion 24 of the tooth 14 as illustrated in FIG. 5. It is important that substantially all of the cementum 52 be removed in this manner from all of the exposed root surface.

Figures 6, 7:
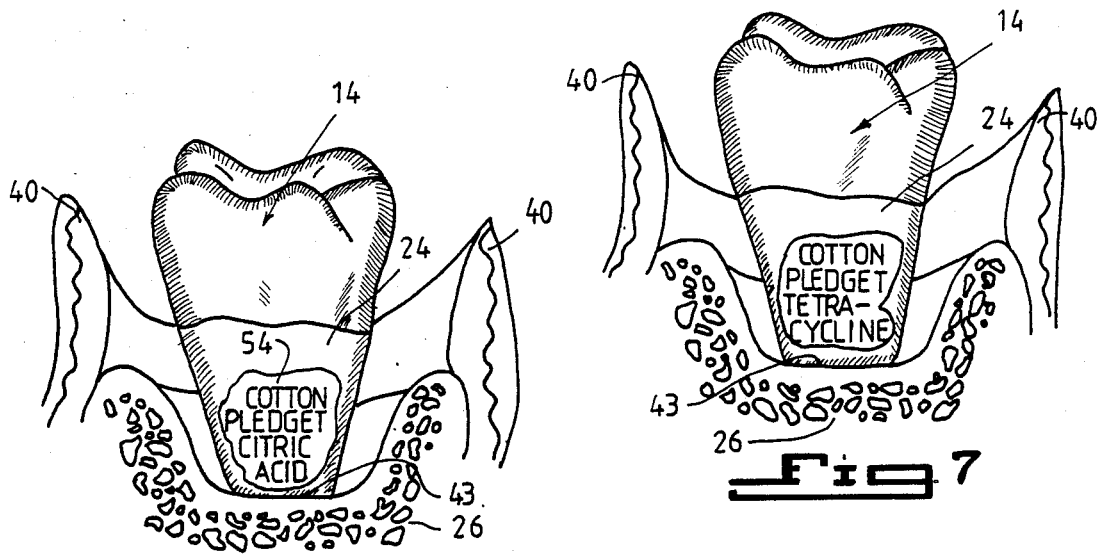
FIG. 6 is a sectional view of the structure set forth in FIGS. 2 through 5 illustrating a further step in the practice of the method of the invention and the use of the composition of the invention.
FIG. 7 is a sectional view of the structure set forth in FIGS. 2 through 6 illustrating a further step in the practice of the method of the invention and the use of the composition of the invention.

The next two steps illustrated in FIGS. 6 and 7 in the method and use of the composition of the invention involve chemical treatment of the surface of the root portion 24 of the tooth 14. In the first chemical step illustrated in FIG. 6 a cotton pledget 54 soaked with citric acid solution is applied to the surface of the root portion 24 of the tooth 14. The citric acid solution is applied to the surface of the root portion 24 through the use of the cotton pledget 54 that is placed against the surface of the root portion 24 for a period of time of substantially one and one-half to substantially three minutes. This treatment with the citric acid solution results in the leaching out of surface calcium and the exposure of decalcified dention. This treatment will encourage subsequent connective tissue attachment to the root portion 24.

As illustrated in FIG. 7, the next step in the chemical treatment portion of the method and the use of the composition of the invention is to chemically treat the surface of the root portion 24 with a Tetracycline solution. As illustrated, this Tetracycline solution is applied to the surface of the root portion 24 by applying a Tetracycline soaked pledget 56 to the surface of the root portion 24 for a period of time between substantially one and one-half to substantially three minutes. The applied solution has substantially a concentration of 1 mg./ml/ of Tetracycline. The effect of this Tetracycline treatment is to further dissolve out calcium from the surface of the root portion 24 and also importantly to leave a residue of Tetracycline on the root portion 24. This Tetracycline residue retards undesired epithelial cell attachment to the surface of the root portion 24 and promotes connective tissue cell attachment to root portion 24.

During the chemical treatment of the surface of the root portion 24 illustrated in FIGS. 6 and 7, saliva contamination of the surface of the root portion 24 must be avoided using techniques known in the art. Otherwise, the chemical treatments may not be effective.

Figure 8:
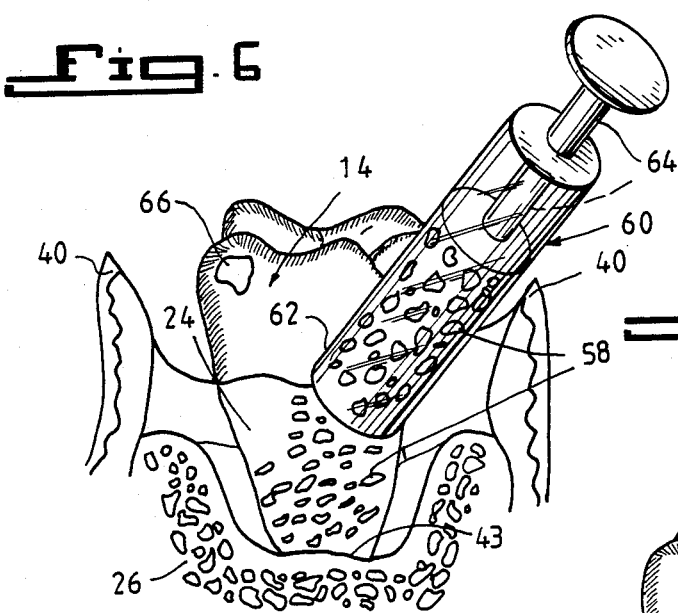
FIG. 8 is a sectional view of the structure set forth in FIGS. 2 through 7 illustrating a further step in the practice of the method of the invention and the use of the composition of the invention.

FIG. 8 illustrates the next step in the practice of the method of the invention and the use of the composition of the invention. In this step, the bony defect 43 is filled with the bone growth promoting composition 58. To fill the bony defect 43 an open ended 1 ml. syringe 60 is filled with the composition 58 and the open end portion 62 is placed adjacent the bony defect 43. Then the plunger 64 of the syringe 60 is pushed inward to expell the composition 58 from the syringe 60 and into the bony defect 43. The bony defect 43 is overfilled with the composition 58. To accomplish this overfilling, saliva 66 from the mouth and blood from the surrounding bone is allowed to come into contact with the composition 58 as the composition 58 is being placed into the bony defect 43. The saliva and blood activate the composition 58 and cause it to stick to itself and also to the treated surface of the root portion 24. This adhesion of the composition 58 to itself and to the treated root portion 24 surface permits the bony defect to be overfilled.

Figure 9:
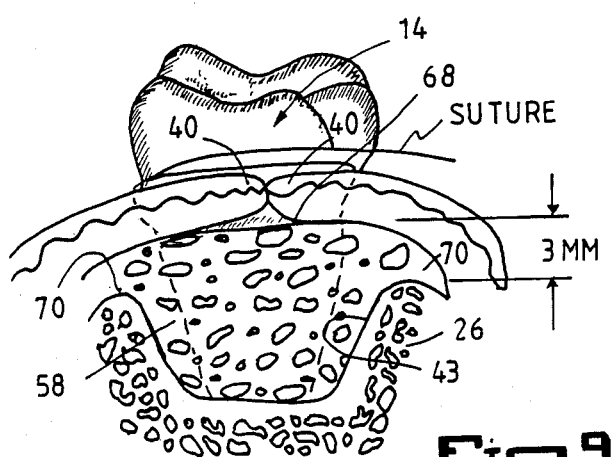
FIG. 9 is a sectional view of the structure set forth in FIGS. 2 through 8 illustrating a further step in the practice of the method of the invention and the use of the composition of the invention.

The next step in the practice of the method of the invention and in the use of the composition of the invention is illustrated in FIG. 9. As illustrated in FIG. 9, the sufficient composition 58 should be added to the bony defect pocket 43 in order that the outer surface 68 of the overfill of the composition 58 is substantially 3 millimeters above the adjacent edges 70 of the bony defect pocket 43. As illustrated in FIG. 9, after this filling the perpheral edges of the flaps 40 are sutured together in a manner well known in the art.

Figure 10:
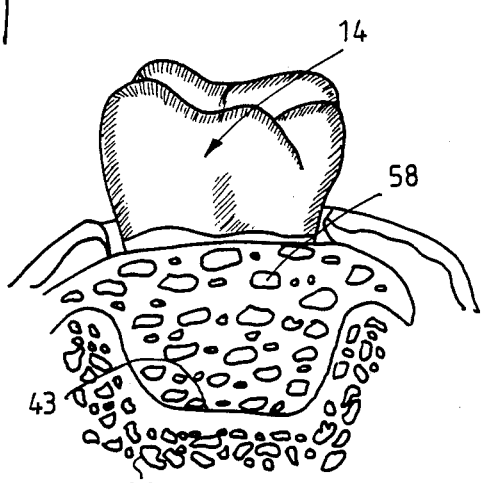
FIG. 10 is a sectional view of the structure set forth in FIGS. 2 through 9 illustrating a step in the healing process associated with practice of the method of the invention and the use of the composition of the invention.

FIGS. 10 through 13 illustrate the healing process involved with the method of the invention and the use of the composition of the invention. As illustrated in FIG. 10, after approximately one week after the previously described surgery, the flap edges 40 die back over the composition 58, but this composition 58 limits the extent of the die back.

Figure 11:
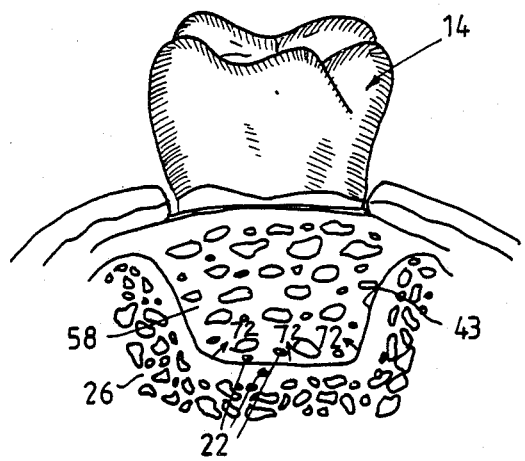
FIG. 11 is a sectional view of the structure set forth in FIGS. 2 through 10 illustrating a further step in the healing process associated with the practice of the method of the invention and the use of the composition of the invention.
Figure 12:
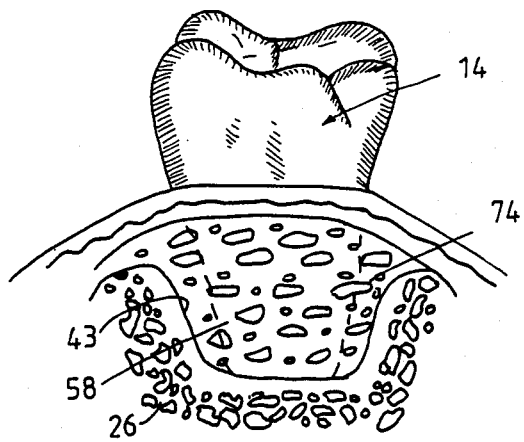
FIG. 12 is a sectional view of the structure set forth in FIGS. 2 through 11 illustrating a further step in the healing process associated with the practice of the method of the invention and the use of the composition of the invention.

FIG. 11 illustrates the healing process approximately one month after the previously described surgery. At this stage in the healing process cells represented by the number 22 from the bone 26 migrate into the composition 58 as represented by the arrows 72. Then as indicated in FIG. 12, three months after the previously described surgical procedure, new bone 74 is noted in the area of the composition 58, the epithelial mono layer 76 thickens followed by the development of connective tissue thickening between the bone 26 and the epithelium. The composition 58 is fully colonized by osteoblasts.

Figure 13:
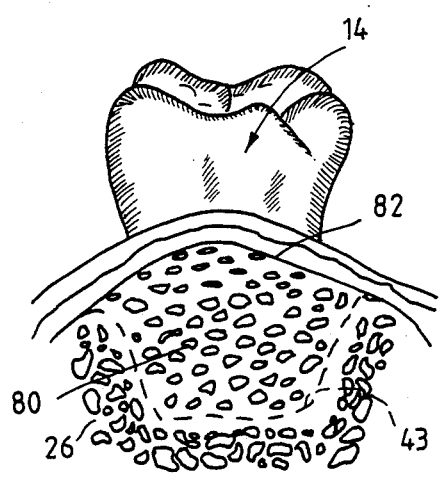
FIG. 13 is a sectional view of the structure set forth in FIGS. 2 through 12 illustrating a further step in the healing process associated with the practice of the method of the invention and the use of the composition of the invention.

FIG. 13 illustrates the healing process some six months to one year after the previously described surgical procedure. It will be noted that the connective tissue interface has widened maximally and that the original bony crater or defect 43 is no longer present. Instead the same area is filled with new bone 80 that has a flat to slightly rounded outer surface 82. At this stage the healing process is essentially complete although bone maturation may continue for some one to two years that will show as increased density in the original bony defect 43 area on x-rays. At this point the method of the invention and the use of the composition 58 would normally be complete.

Figure 14:
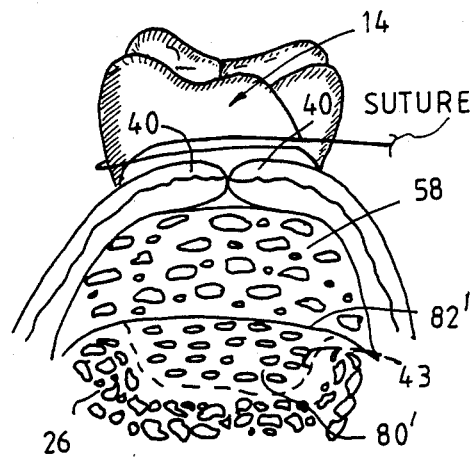
FIG. 14 is a sectional view of the structure set forth in FIGS. 2 through 13 illustrating the final step in the practice of the method of the invention and the use of the composition of the invention.

In some cases the bony defect 43 may be very deep and require extensive growth of new bone to fill it. In this case, further steps in the method are necessary. These steps are indicated in FIG. 14. As indicated in FIG. 14, it is possible to repeat the process previously described and set forth in FIGS. 2 through 9. In doing this the composition 58 is placed on top of the surface 82' of the previously grown new graft bone 80'. This can be performed from substantially six months to substantially one year after the initial previously described surgical procedure has been completed.

Figure 15:
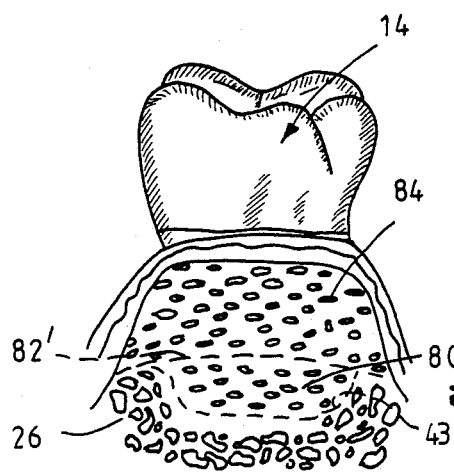
FIG. 15 is a sectional view of the structure set forth in FIGS. 2 through 14 illustrating the final result of the method and the use of the composition of the invention.

FIG. 15 illustrates how the graft area looks approximately one year after the second operation illustrated in FIG. 14. As indicated, a second outer layer of bone 84 is present above the outer surface 82 of the bone 80 resulting from the first procedure illustrated in FIGS. 2 through 9.

The citric acid solution used in the previously described method is a 1M water solution. It appears that this 1M citric acid solution accomplishes the following:
a. exposes root collagen,
b. denatures root cementum absorbed bacterial endotoxin,
c. removes the "smear layer" left by hand and rotary instruments after mechanical root preparation (scaling and root planing),
d. sterilizes root surfaces, and
e. denatures root collagen (hypothesis) making the roots more desirable for fibronectin seating.

The previously mentioned Tetracycline solution is a 1 mg./ml. water solution. The bone graft composition 58 used in the previously described method is as follows:

Hydroxyapatite (20 to 40 mesh) -1 gm
Hydroxyapatite (40 to 60 mesh) -0.5 gm
Freeze dried decalcified human bone - 1 gm
Tetracycline - 200 mg
Fibronectin - aqueous solution (from 5µg/ml to 50 µg/ml concentration) -3 ml These ingredients are thoroughly mixed prior to the composition 58 being used in the previously described method. This mixing must take place about a minimum of 15 minutes prior to use.

As far as it is understood, the purposes of each of the components of the bone graft composition are as follows:

1. Freeze dried declacified bone - FDDBA (raw bone morphologic protein BMP)
   a. As a source of raw collagen it acts as a hemostatic agent by activating the extrinsic clotting system.
   b. In the preferred mixture cortical FDDBA as opposed to cancellous FDDBA is used. Cortical FDDBA has an unpublished characteristic of causing epithelial "die back", i.e. it is at least partially inhibitory of epithelial growth.
   c. It attracts osteoblasts (chemotaxis) and stimulates them to secrete bone.
2. HA (Hydroxyapatite)
   a. Gives structural support to the graft mixture preventing collagen collapse resulting in residual defect formation post grafting. Two sizes of HA are used to create interparticulate intersticies into which cells and blood vessels could grow. Commercial periodontal HA is too small and does not allow proper in growth.
   b. Has a hydrophillic surface which will react (absorb or adhere) with whatever chemical it contacts first.
   c. Once coated or activated chemically each HA particle becomes a cell growth site.
   d. Two sizes of HA are used 20–40 mesh and 40–60 mesh. Although a single size coralene HA with appropriate intertices may be alternatively used. The HA intertices created by the large particles are partially again filled by the smaller particles. The collagen and cells forming in these spaces and attached to the HA particle surfaces cannot contract as would normally occur.
3. Tetracycline
   a. Antibiotic effect
      (1) Graft material storage preservative.

(2) Direct antibacterial effect on oral plaque (bacteria) during wound healing, avoiding graft contamination.

(3) Long term slow release mechanism due to its biochemical affinity to bone prevents reinfection by bacteria of graft sites and eliminates deep bacterial contamination of the graft site.

b. Antimetabolite effect generally slows cell function during cell turn over. This is good as it restricts aberrant cell overgrowth. The Tetracycline in effect calms the cells down and has them produce product (bone and collagen) rather than just rapidly and destructively reproducing.

c. Tetracycline preferentially retards epithelial cell growth versus connective tissue cell growth. This effect plus the effect of the cortical bone factor yields an initial skin (epithelium) "die back" post surgery allowing connective tissue proliferation into the graft material. Tetracycline pretreatment of the roots slows epithelial repopulation and downgrowth and preferentially allows connective tissue cell growth and attachment. cell growth and attachment.

d. Tetracycline in acid solution also acts to decalcify root surfaces.

4. Fibronectin (a cell attachment molecule)

a. Mediates cell to cell adhesion and attachment.

b. Mediates cell to substrate adhesion and attachment.

c. Orients fibroblasts to lay down collogen optimally in wound healing.

d. Has attachment sites for fibrin and heprin (main constituents of blood clots). Thus orients cells for proper healing.

e. As the graft mixture fluid (20% fibronectin) is the first chemical to touch the pretreated root surface. The fibronectin optimally allows fibrin attachment to the root surface a precursor to connective tissue reattachment.

f. Fibronectin attaches preferentially to denatured collagen such as that produced by the 1 ml citric acid root pre treatment.

g. Fibronectin when activated by glycoaminoglycans (GAG) in saliva cause jelling of all components treated by the fibronectin giving the graft material an inherent "body" and an ability to stick to whatever surface it touches.

All working together, these ingredients of the bone graft composition 58 fill periodontal bony defects and allow supracrestal augmentation by giving cells a treated matrix into which they are attracted to grow, adhere and proliferate while simultaneously excluding epethelial downgrowth. They also effect direct cell product activity and control bacterial contamination both pre and post surgery and long term in grafted areas.

It has been determined that the previously described bone growing method can be enhanced by the addition of the final method step of orally administering or providing post surgical oral nutrients to the surgical bone graft patient after the completion of the last surgical step in the previously described bone growing method. These post surgical nutrients and the dosage are set forth below:

| Nutrient Type and Size | Dosage |
| --- | --- |
| 1 gm Vitamin C | Take 500 mg twice a day. |
| 1 gm Tryptophane | Take 1 gm one to two times daily, particularly at bedtime. |
| .5 gm Choline | Take 2 gms the evening after the surgery. After that take 500 mg once a day. |
| 1 gm Calcium | Take 500 mg twice a day. |
| 400 mg Vitamin E | Take 400 mg once a day. |

The foregoing should be taken for a one month period following surgery.

The following suggested procedures though they are not essential to the practice of the method and the use of the composition 58, have been found to give good results and hence are recommended. The bone growing composition 58 should be prepared at least one-half hour prior to its use. This is accomplished by mixing the Fibronectin solution with the rest of the bone growing composition.

It is recommended that the graft sites be prepared in the standard fashion for osseous graft procedures. A "modified Widman" papillary saving, or Takei type flap design is recommended. Osseous lesions are to be completely debrided of connective tissue and granulation tissue. Bone fenestration into walls of the defects is optional. Tooth roots should be prepared to thoroughly remove all bacteria, calculus, and bacterially affected or hypercalcified cementum.

The graft material composition 58 is loaded into the syringe 60 by tamping the open barrel of the syringe 60 into the mixed graft material 58. After injecting the material into the defect, it should be further packed in place. Additional material may be added as needed or desired. Attempt at supracrestal augmentation is encouraged.

As close to primary closure as reasonably possible is recommended using verticle mattress papillary suturing technique in either an interrupted or continuous manner. Graft sites are to be covered for one week using a suitable periodontal dressing such as COE Pak, Zone, etc.. Repacking a second week may be done at the judgment of the practitioner.

The recommended post surgical hygiene maintenance sequence is as follows: first two visits at one month intervals, then two months, and then every three months. A plaque index is recommended to numerically document plaque levels and as a basis for prescription of antiplaque agents. Recommended post surgical medications are as follows: Tetracycline 250 mg QID X 2 weeks, Motrin 400–600 mg QID X 2 days. It is also recommended that the patient be given the antibiotic Tetracycline and the Motrin and Tylenol for pain after surgery.

The foregoing bone growing method and the bone growing composition 58 have been used successfully on a large number of patients that needed bone regeneration next to their teeth. Using this bone growing method and the composition 58 resulting in only very minimal shrinkage of the flap height against the adjacent tooth. This can be traced to the good bony defect fill of the composition 58 and also the ability to pile up the composition 58. This method also promotes bone proliferation and cell growth of bone cells by retarding gingival connective tissue growth. This retardation takes place predominately during substantially the first three weeks after surgery.

The bone growing method and the use of the bone growing composition 58 have been previously described in connection with their use in the human mouth. However, with appropriate apparent modifications the method 58 can be used in connection with other locations in the human body and can also be used in non-human living creatures.

Although the invention has been described with reference to certain preferred embodiment, it will be understood that variations and modifications may be made within the spirit and scope of the invention as defined in the appended claims.

What is claimed is:

1. A method of promoting the growth of bone in a living creature comprising the steps of:
   a. providing a first size of hydroxyappetite;
   b. providing a second size of hydroxyappetite;
   c. providing fibronectin;
   d. providing a source of collagen;
   e. mixing said first size hydroxyappetite, said second size hydroxyappetite, said source of collagen and said fibronectin to form a graft composition;
   f. surgically operating on the living creature to expose living bone;
   g. inserting said graft composition adjacent said living bone to treat said living bone after said living bone has been surgically exposed; and
   h. surgically covering said living bone and said adjacently located graft composition.

2. The method of promoting growth of bone of claim 1, wherein said living creature has a mouth and said step of surgically operating on the living creature to expose living bone comprises surgically operating on the mouth of said living creature.

3. The method of promoting growth of bone of claim 2 wherein the mouth of said living creature has at least one tooth having a root and said step of surgically operating on the living creature to expose living bone also comprises surgically operating to expose the root of said tooth.

4. The method of promoting growth of bone of claim 3 further comprising the step of preparing the surface of the root of said tooth by using an abrasive after the step of surgically operating to expose living bone and the root of said tooth.

5. The method of promoting growth of bone of claim 4 further comprising the step of applying a solution to the root of said tooth to remove any smear layer after the step of preparing the root of said tooth by using an abrasive.

6. The method of promoting growth of bone of claim 5 wherein said step of inserting said graft composition adjacent said living bone also comprises covering the surface of the root of said tooth with said graft composition to provide for reattaching bone to the tooth.

7. The method of promoting growth of bone of claim 6 further comprising the steps of providing a syringe, inserting said graft composition in said syringe after said graft composition is formed, and wherein said step of inserting said graft composition is accomplished through the use of said syringe.

8. The method of promoting growth of bone of claim 6 wherein said step of inserting said graft composition comprises inserting additional graft composition to bring the level of graft composition beyond that of the adjacent living bone.

9. The method of promoting growth of bone of claim 8 further comprising the step of administering a nutrient after said step of covering said living bone and said adjacently located graft composition.

10. The method of promoting growth of bone of claim 9 wherein said step of administering a nutrient comprises administering at least one vitamin.

11. The method of promoting growth of bone of claim 9 wherein said step of administering a nutrient comprises administering at least one mineral.

12. The method of promoting growth of bone of claim 1 further comprising repeating the steps a. through h. in claim 17 to promote further growth of bone adjacent previously grown bone.

* * * * *